__US009700412B2__

(12) United States Patent
Yaron et al.

(10) Patent No.: US 9,700,412 B2
(45) Date of Patent: Jul. 11, 2017

(54) HEART VALVE REPAIR DEVICES FOR PLACEMENT IN VENTRICLE AND DELIVERY SYSTEMS FOR IMPLANTING HEART VALVE REPAIR DEVICES

(71) Applicant: MITRALIX LTD., Rehovot (IL)

(72) Inventors: Ira Yaron, Har Adar (IL); Yonatan Ben-Zvi, Kiryat Tiv'on (IL)

(73) Assignee: MITRALIX LTD., Rehovot (IL)

( * ) Notice: Subject to any disclaimer, the term of this patent is extended or adjusted under 35 U.S.C. 154(b) by 0 days.

(21) Appl. No.: 14/315,749

(22) Filed: Jun. 26, 2014

(65) Prior Publication Data

US 2015/0374493 A1    Dec. 31, 2015

(51) Int. Cl.
    *A61F 2/24*    (2006.01)

(52) U.S. Cl.
    CPC .......... *A61F 2/2445* (2013.01); *A61F 2/2442* (2013.01); *A61F 2/2466* (2013.01); *A61F 2/2457* (2013.01); *A61F 2230/0091* (2013.01)

(58) Field of Classification Search
    CPC ........................... A61F 2/2442; A61F 12/2445
    USPC ................................................ 623/2.36–2.37
    See application file for complete search history.

(56) References Cited

U.S. PATENT DOCUMENTS

| | | |
|---|---|---|
| 2,108,206 A | 2/1938 | Meeker |
| 3,378,010 A | 4/1968 | Codling et al. |
| 4,602,911 A | 7/1986 | Ahmadi et al. |
| 4,972,874 A | 11/1990 | Jackson |
| 5,350,397 A * | 9/1994 | Palermo ........... A61B 17/12022 128/898 |
| 5,593,424 A | 1/1997 | Northrup, III |
| 5,810,882 A | 9/1998 | Bolduc et al. |
| 6,183,512 B1 | 2/2001 | Howanec, Jr. et al. |

(Continued)

FOREIGN PATENT DOCUMENTS

| | | |
|---|---|---|
| EP | 2 072 027 A1 | 6/2009 |
| EP | 2072027 A1 | 6/2009 |
| WO | 00/47139 A1 | 8/2000 |
| WO | 00/60995 A2 | 10/2000 |
| WO | WO 00/60995 * | 10/2000 |
| WO | 03/020179 A1 | 3/2003 |

(Continued)

OTHER PUBLICATIONS

European Patent Office, International Search Report and Written Opinion in International Application No. PCT/IB2012/001263, dated Jan. 7, 2013.

(Continued)

*Primary Examiner* — Thomas J Sweet
*Assistant Examiner* — Leslie Lopez
(74) *Attorney, Agent, or Firm* — Kacvinsky Daisak Bluni PLLC; Douglas E. Ringel

(57) ABSTRACT

Devices and methods for the repair of the functioning of heart valves are provided. A device may comprise a ventricular winding having a generally spiral shape, wherein the device is free of any atrial stabilizing section. A method involves positioning the device such that chords associated with the heart valve are positioned within the path of the generally spiral shape of the ventricular winding and turning the ventricular winding such that the chords move closer to the center of the ventricular winding. The ventricular winding draws the chords closer together, thereby pulling the valve leaflets closer together in order to facilitate their coaptation and proper closing. A delivery system for maneuvering and releasing a heart valve repair device comprises an applicator tube and internal rod.

26 Claims, 7 Drawing Sheets

(56) References Cited

U.S. PATENT DOCUMENTS

| | | |
|---|---|---|
| 6,217,610 B1 | 4/2001 | Carpentier et al. |
| 6,332,893 B1 | 12/2001 | Mortier et al. |
| 6,348,068 B1 | 2/2002 | Campbell et al. |
| 6,371,464 B1 | 4/2002 | Porche et al. |
| 6,425,916 B1 | 7/2002 | Garrison et al. |
| 6,454,799 B1 | 9/2002 | Schreck |
| 6,461,366 B1 | 10/2002 | Seguin |
| 6,544,272 B1 | 4/2003 | Jakob et al. |
| 6,629,534 B1* | 10/2003 | St. Goar ............ A61B 17/0469 128/898 |
| 6,730,118 B2 | 5/2004 | Spenser et al. |
| 6,752,813 B2 | 6/2004 | Goldfarb et al. |
| 6,770,083 B2 | 8/2004 | Seguin |
| 6,786,924 B2 | 9/2004 | Ryan et al. |
| 6,797,002 B2 | 9/2004 | Spence et al. |
| 6,893,460 B2 | 5/2005 | Spenser et al. |
| 7,048,754 B2 | 5/2006 | Martin et al. |
| 7,077,861 B2 | 7/2006 | Spence |
| 7,166,127 B2 | 1/2007 | Spence et al. |
| 7,189,199 B2 | 3/2007 | McCarthy et al. |
| 7,226,467 B2 | 6/2007 | Lucatero et al. |
| 7,288,097 B2 | 10/2007 | Séguin |
| 7,316,706 B2 | 1/2008 | Bloom et al. |
| 7,544,206 B2 | 6/2009 | Cohn |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Séguin |
| 7,691,143 B2 | 4/2010 | Wright et al. |
| 7,699,892 B2 | 4/2010 | Rafiee et al. |
| 7,704,269 B2 | 4/2010 | St. Goar et al. |
| 7,736,388 B2 | 6/2010 | Goldfarb et al. |
| 7,753,923 B2 | 7/2010 | St. Goar et al. |
| 7,803,187 B2 | 9/2010 | Hauser |
| 7,811,296 B2 | 10/2010 | Goldfarb et al. |
| 7,896,915 B2 | 3/2011 | Guyenot et al. |
| 7,951,195 B2 | 5/2011 | Antonsson et al. |
| 7,967,857 B2 | 6/2011 | Lane |
| 8,128,691 B2 | 3/2012 | Keränen |
| 8,968,393 B2 | 3/2015 | Rothstein |
| 8,998,933 B2 | 4/2015 | Rothstein et al. |
| 2001/0034551 A1 | 10/2001 | Cox |
| 2001/0041933 A1 | 11/2001 | Thoma |
| 2002/0013571 A1 | 1/2002 | Goldfarb et al. |
| 2002/0035361 A1 | 3/2002 | Houser et al. |
| 2002/0151970 A1 | 10/2002 | Garrison et al. |
| 2002/0183766 A1 | 12/2002 | Seguin |
| 2003/0149476 A1 | 8/2003 | Damm et al. |
| 2003/0167071 A1 | 9/2003 | Martin et al. |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0049207 A1 | 3/2004 | Goldfarb et al. |
| 2004/0087975 A1 | 5/2004 | Lucatero et al. |
| 2004/0092962 A1 | 5/2004 | Thornton et al. |
| 2004/0162610 A1 | 8/2004 | Liska et al. |
| 2004/0225300 A1 | 11/2004 | Goldfarb et al. |
| 2004/0236354 A1 | 11/2004 | Seguin |
| 2004/0267357 A1 | 12/2004 | Allen et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0075659 A1 | 4/2005 | Realyvasquez et al. |
| 2005/0143811 A1 | 6/2005 | Realyvasquez |
| 2005/0149014 A1 | 7/2005 | Hauck et al. |
| 2005/0240202 A1 | 10/2005 | Shennib et al. |
| 2006/0020275 A1 | 1/2006 | Goldfarb et al. |
| 2006/0089671 A1 | 4/2006 | Goldfarb et al. |
| 2006/0135993 A1 | 6/2006 | Seguin |
| 2006/0184203 A1 | 8/2006 | Martin et al. |
| 2006/0195134 A1 | 8/2006 | Crittenden |
| 2006/0276871 A1 | 12/2006 | Lamson et al. |
| 2006/0282161 A1 | 12/2006 | Huynh et al. |
| 2007/0078297 A1 | 4/2007 | Rafiee et al. |
| 2007/0100356 A1 | 5/2007 | Lucatero et al. |
| 2007/0112421 A1 | 5/2007 | O'Brien |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0255396 A1* | 11/2007 | Douk .................. A61B 17/083 623/2.1 |
| 2008/0051703 A1 | 2/2008 | Thornton et al. |
| 2008/0051807 A1 | 2/2008 | St. Goar et al. |
| 2008/0071365 A1 | 3/2008 | Ley |
| 2008/0097489 A1 | 4/2008 | Goldfarb et al. |
| 2008/0167702 A1 | 7/2008 | Ransbury et al. |
| 2008/0167714 A1 | 7/2008 | St. Goar et al. |
| 2008/0183194 A1 | 7/2008 | Goldfarb et al. |
| 2008/0208330 A1 | 8/2008 | Keränen |
| 2008/0228272 A1 | 9/2008 | Moaddeb et al. |
| 2009/0105815 A1 | 4/2009 | Krever et al. |
| 2009/0156995 A1 | 6/2009 | Martin et al. |
| 2009/0163934 A1 | 6/2009 | Raschdorf, Jr. et al. |
| 2009/0198322 A1 | 8/2009 | Deem et al. |
| 2009/0198324 A1 | 8/2009 | Orlov |
| 2009/0222026 A1 | 9/2009 | Rothstein et al. |
| 2009/0259210 A1 | 10/2009 | Sabbah |
| 2009/0270858 A1 | 10/2009 | Hauck et al. |
| 2009/0299471 A1* | 12/2009 | Keranen ............... A61F 2/2445 623/2.37 |
| 2009/0326567 A1 | 12/2009 | Goldfarb et al. |
| 2010/0010538 A1 | 1/2010 | Juravic et al. |
| 2010/0016958 A1 | 1/2010 | St. Goar et al. |
| 2010/0022823 A1 | 1/2010 | Goldfarb et al. |
| 2010/0023118 A1 | 1/2010 | Medlock et al. |
| 2010/0094317 A1 | 4/2010 | Goldfarb et al. |
| 2010/0100108 A1 | 4/2010 | Goldfarb et al. |
| 2010/0130924 A1 | 5/2010 | Martin et al. |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0191256 A1 | 7/2010 | Séguin |
| 2010/0204662 A1 | 8/2010 | Orlov et al. |
| 2010/0210899 A1 | 8/2010 | Schankereli |
| 2010/0217283 A1 | 8/2010 | St. Goar et al. |
| 2010/0262167 A1 | 10/2010 | Jelich et al. |
| 2010/0280603 A1 | 11/2010 | Maisano et al. |
| 2010/0298929 A1 | 11/2010 | Thornton et al. |
| 2010/0298930 A1 | 11/2010 | Orlov |
| 2010/0331971 A1* | 12/2010 | Keranen et al. ............ 623/2.11 |
| 2011/0004227 A1 | 1/2011 | Goldfarb et al. |
| 2011/0029055 A1 | 2/2011 | Tidemand |
| 2011/0054306 A1 | 3/2011 | del Nido et al. |
| 2011/0071626 A1 | 3/2011 | Wright et al. |
| 2011/0077733 A1 | 3/2011 | Solem |
| 2013/0006352 A1* | 1/2013 | Yaron .................. A61F 2/2445 623/2.37 |
| 2014/0163669 A1 | 6/2014 | Ben-Zvi et al. |
| 2014/0194975 A1 | 7/2014 | Quill et al. |
| 2015/0032204 A1 | 1/2015 | Johansson |

FOREIGN PATENT DOCUMENTS

| | | |
|---|---|---|
| WO | 2004/112651 A2 | 12/2004 |
| WO | 2005/087139 A1 | 9/2005 |
| WO | 2006/091163 A1 | 8/2006 |
| WO | 2007/030063 A1 | 3/2007 |
| WO | 2011/057087 A1 | 5/2011 |
| WO | 2012/094406 A1 | 7/2012 |
| WO | 2012/095116 A1 | 7/2012 |

OTHER PUBLICATIONS

Paul T. L. Chiam, MBBS, et al., "Percutaneous Transcatheter Mitral Valve Repair, a Classification of the Technology," JACC: Cardio-

(56) References Cited

OTHER PUBLICATIONS vascular Interventions, vol. 4, No. 1, 2011, pp. 1-13, published by Elsevier Inc., Jan. 2011.
Mitral Valve Information from <http://www.mitralvalverepair.org/>, Mount Sinai Medical Center, Department of Cardiothoracic Surgery, New York, NY (last updated Jan. 2011).
Gregg W. Stone, MD, "Overview of Percutaneous Mitral Valve Therapies," Columbia University Medical Center, the Cardiovascular Research Foundation (31 pages) (2009).
International Search Report and Written Opinion of the International Searching Authority in International Application No. PCT/IB2015/001026, mailed Oct. 23, 2015.
European Patent Office, International Search Report in related International application No. PCT/IB2015/001026, mailed Oct. 23, 2015, 14 pages.

\* cited by examiner

HEART VALVE REPAIR DEVICES FOR PLACEMENT IN VENTRICLE AND DELIVERY SYSTEMS FOR IMPLANTING HEART VALVE REPAIR DEVICES

FIELD OF THE INVENTION

The invention relates to devices and methods for the repair of the functioning of heart valves, in particular the mitral valve.

BACKGROUND OF THE INVENTION

Heart valves regulate the movement of blood into and out of the chambers of the heart. The mitral valve, positioned between the left atrium and the left ventricle, can be subject to a condition known as mitral regurgitation, in which the mitral valve does not close properly and some backflow of blood occurs from the left ventricle back into the left atrium. For example, a mitral valve leaflet can experience prolapse during systole, thereby inhibiting leaflet coaptation and permitting backflow of blood into the left atrium.

Various procedures and devices have been proposed to address the condition of mitral regurgitation. For example, some mitral valve repair procedures involve removing a section of a valve leaflet in order to reduce its propensity for prolapse. Other procedures involve mitral valve replacement. The MITRACLIP (Abbott Vascular) is a device intended to be positioned across the mitral valve to create a double orifice, in an effort to allow the valve to close fully during systole.

US 2010/0331971 discloses cardiac valve downsizing devices and methods. The objective of these downsizing devices is to downsize the annulus of the valve by circumflexing all or substantially all of the chords. A downsizing device as disclosed in US 2010/0331971 is formed as a helix wherein a lower part of the helix is designed to extend on the ventricular side of the valve along an outer periphery adjacent the heart wall around the outermost chords. This outer periphery is accessed by extending the helix through a commissure at the periphery of the valve or through the annulus itself. Rotating the helix causes advancement of the helix so that part of the helix extends into the ventricle at the outer periphery around the outermost chords, while part of the helix is in the atrium, adjacent the annulus, thereby anchoring the device with respect to the atrium.

The Applicant's prior application US 2013/0006352 also relates to devices and methods for the repair of the functioning of heart valves. US 2013/0006352 discloses heart valve repair devices designed to draw the desired leaflet edge areas together. A device as disclosed in US 2013/0006352 comprises a first section having a generally spiral shape, with the spiral shape emanating from a center of the spiral, and a second section connected to the first section at the center of the first section. The first section is positioned on the ventricular side of the heart valve, with the selected chords positioned within the path of the generally spiral shape, and the second section is positioned on the atrial side of the heart valve. US 2013/0006352 discloses that, in a device as described therein, the ventricular section draws the captured chords together, thereby pulling the desired valve leaflet areas together, while the atrial section stabilizes or anchors the device relative to the atrium.

There is a continuing need for improved treatment for mitral valve regurgitation and for the repair of the functioning of heart valves in general. The various procedures and devices previously proposed can be improved upon in terms of their overall clinical outcome, ease of use, reduction of procedure time and risk, and/or reduction of cost.

SUMMARY OF THE INVENTION

The present invention provides devices and methods for the repair of the functioning of heart valves.

In prior heart valve repair devices for capturing leaflet chords as exemplified in certain prior devices as discussed above, the devices have included parts or sections for anchoring the devices relative to the atrium, in order to ensure that the devices remained stable in the heart once implanted. The inventive heart valve repair devices as described herein depart from these prior teachings. A heart valve repair device as described herein comprises a ventricular winding for capturing leaflet chords and drawing them together, without having any connected atrial stabilizing section that stabilizes or anchors the device relative to the atrium. The device, without any atrial stabilizing section, has freedom to move with respect to the atrium, providing previously unrecognized advantages as described below that could not be attained by prior devices that were anchored to the atrium. While prior devices as discussed above have included atrial anchoring in order to ensure stability after implantation, the inventors have found, in both ex vivo testing and in vivo animal testing, that a device as described herein with a ventricular winding and without a connected atrial stabilizing section is sufficiently held in place by the interaction between the ventricular winding and the chords, thereby allowing the device to be practiced without a connected atrial stabilizing section, realizing advantages as described herein.

In some embodiments, the implantable heart valve repair device comprises, consists essentially of, or consists of a ventricular winding having a generally spiral shape adapted to be positioned on a ventricular side of the heart valve such that chords associated with the heart valve are positioned within the path of the generally spiral shape of the ventricular winding. The ventricular winding is designed to draw chords associated with the heart valve closer together, thereby pulling the valve leaflets closer together in order to facilitate their coaptation and proper closing. The implantable heart valve repair device in these embodiments is "free of any atrial stabilizing section," meaning that the device does not have any part that is adapted to stabilize the device by engaging tissue on the atrial side of the valve, such as the wall of the atrium or the annulus of the valve on the atrial side.

In some embodiments, the implantable heart valve repair device has a stabilizing section that consists only of a ventricular stabilizing section that is adapted to engage tissue only on the ventricular side of the valve. The ventricular stabilizing section may consist essentially of, or consist only of, or may be in the form of a ventricular winding having a generally spiral shape as described above for drawing chords associated with the heart valve together. The ventricular winding is adapted to engage tissue only on the ventricular side of the valve, and the ventricular winding stabilizes the device by the interaction between the ventricular winding and the chords on the ventricular side of the valve.

In some embodiments, the implantable heart valve repair device may include a grasping element for facilitating grasping and maneuvering the device during implantation. In some embodiments, the implantable heart valve repair device may include an end portion that is bent downwardly from the general plane of the ventricular winding. In some embodiments, the implantable heart valve repair device may include one or more anti-rotation elements for resisting a backwards rotation of the ventricular winding.

In some embodiments of a method of repairing a heart valve, a heart valve repair device is delivered to the area of the heart valve, wherein the device comprises, consists essentially of, or consists of a ventricular winding having a generally spiral shape. The method further includes positioning the ventricular winding on a ventricular side of the heart valve such that chords associated with the heart valve are positioned within the path of the generally spiral shape of the ventricular winding. The step of positioning the ventricular winding may further include turning the ventricular winding in a first direction such that the chords move closer to the center of the ventricular winding. This movement of the chords pulls the valve leaflets closer together in order to facilitate their coaptation and proper closing. The method may be practiced with a heart valve repair device that is free of any atrial stabilizing section, as described above.

In some embodiments of a delivery system for implanting a heart valve repair device, the delivery system comprises an applicator tube and an internal rod within the applicator tube. The internal rod may be adapted to hold the heart valve repair device during maneuvering of the device. The delivery system is adapted to release the heart valve repair device after positioning of the heart valve repair device in the desired location. The delivery system may include a window through which all or part of the heart valve repair device may be ejected. The delivery system may also include a ramp surface for facilitating ejection of the heart valve repair device.

DETAILED DESCRIPTION

The Applicant's prior application US 2013/0006352 discloses various heart valve repair devices and methods of implanting them. The disclosure of US 2013/0006352 is hereby expressly incorporated herein by reference.

Certain embodiments of heart valve repair devices and methods of using them are described herein with reference to the accompanying drawings. These embodiments are only examples, as numerous variations of the invention disclosed herein are possible within the scope of the appended claims.

Figure 1:
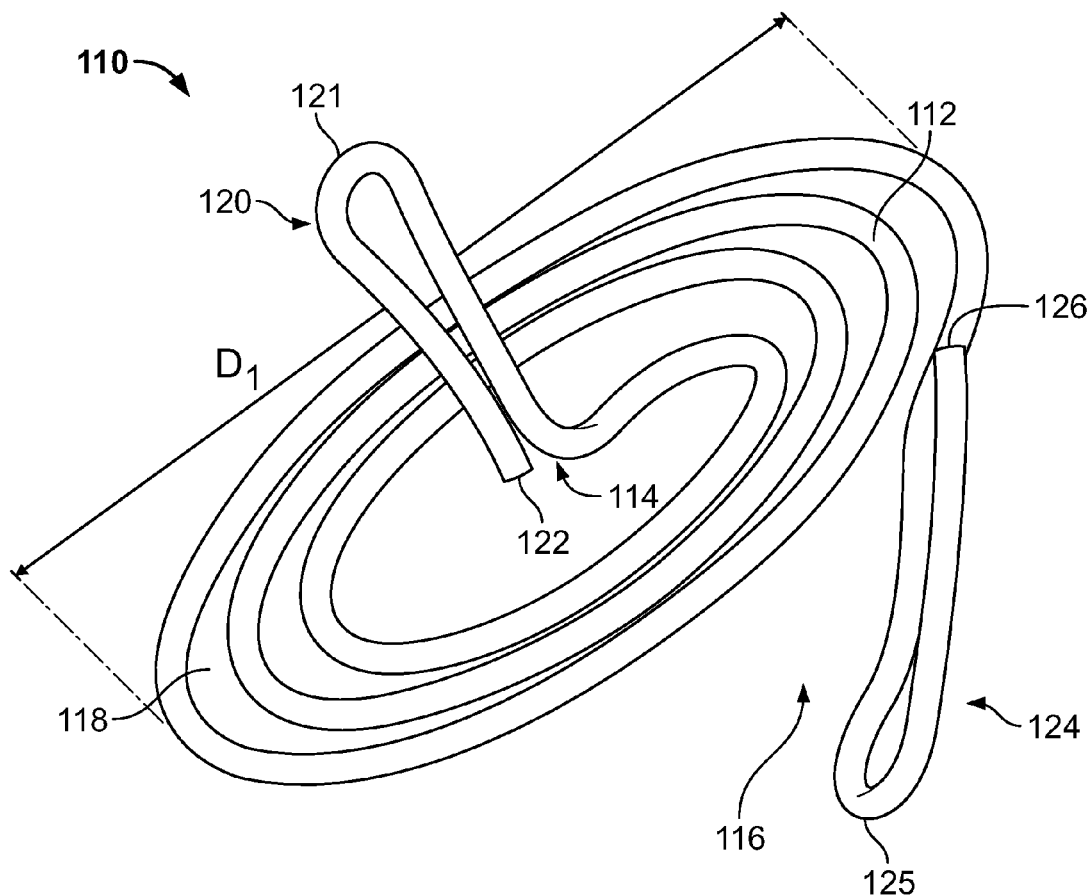
FIG. 1 shows a perspective view of an embodiment of a heart valve repair device.

FIG. 1 shows a first embodiment of a heart valve assisting device 110. The device 110 comprises a ventricular winding 112 and a grasping element 120. As described below, the ventricular winding 112 serves the functions of both facilitating valve leaflet coaptation and stabilizing or anchoring the device with respect to the chords.

The term "spiral" is used herein to refer broadly to shapes defined by a structure forming a winding around a center wherein the winding gradually moves away from the center as it winds around the center. The structure of the winding may begin or emanate from an area at or near the center of the winding. The winding may move away from the center at a constant rate or at a non-constant rate, and the general outline of the spiral may take various shapes, such as substantially circular, substantially elliptical, or other shapes. The spiral may be symmetrical or asymmetrical, and the center around which the winding structure winds may be a point at the geometric center of the spiral or a point that is offset from the geometric center of the spiral. The winding may be in one plane, such that the spiral is substantially flat. Alternatively, the winding may not be in one plane, with the winding moving up or down at a constant or non-constant rate. Thus, for example, the spiral may be substantially conical. The winding may make multiple turns around the center or less than a full turn around the center. The winding structure of the spiral forms a path that starts from an opening at the outer periphery of the spiral and that moves toward the center of the spiral as the path winds around the center of the spiral.

As can be seen in FIG. 1, the ventricular winding 112 has a generally spiral shape. The spiral shape is defined by the wire structure of the ventricular winding 112 forming a winding around a center 114 of the ventricular winding 112, wherein the wire structure of the winding begins or emanates from an area at or near the center 114 and gradually moves away from the center 114 as it winds around the center 114. In the case of FIG. 1, the winding of the ventricular winding 112 moves away from the center 114 at a generally constant rate, and the general outline of the spiral of the ventricular winding 112 has a substantially circular shape.

In the embodiment of FIG. 1, the ventricular winding 112 is generally in one plane, with an end portion 124 of the ventricular winding 112 being bent or angled downwardly as shown. In an alternative embodiment, the ventricular winding 112 may move gradually out of plane.

As shown in FIG. 1, the winding structure of the ventricular winding 112 forms a path 118 that starts from an opening 116 at the outer periphery of the spiral and that moves toward the center 114 of the spiral as the path 118 winds around the center 114 of the spiral. In this illustrated embodiment, the path 118 comprises about three turns around the center 114. More or fewer turns may be used.

As described above, the spiral may take other shapes. In addition, the ventricular winding may be comprised of more than one spiral. For example, the ventricular winding may have two, three, four, or more spirals, which may be similar or dissimilar to each other. In one example, two spirals may emanate from a common center, each being similar to the other except that each starts in a direction that is 180 degrees from the other. This example results in nested spirals in which the opening of each of the spirals is 180 degrees from the opening of the other spiral. In other examples, three spirals may emanate from a common center, starting 120 degrees apart and having openings 120 degrees apart, or four spirals may emanate from a common center, starting 90 degrees apart and having openings 90 degrees apart.

The overall diameter D1 of the ventricular winding may be substantially smaller than the diameter of the annulus of the valve. This enables maneuvering the ventricular winding to capture only selected groups of chords, in order to pull together desired areas of the valve leaflets. For example, the overall diameter D1 of the ventricular winding 112 may be approximately 1.0-2.0 centimeters (e.g., 1.2, 1.5, or 1.8 centimeters), but larger or smaller diameters are possible.

At its outer end, the ventricular winding 112 terminates at the end portion 124. In the embodiment of FIG. 1, the end portion 124 is bent downwardly from the general plane of the ventricular winding 112. The end portion 124 is formed as a loop of the wire structure of the ventricular winding 112, connected at junction 126. In this manner, the end portion 124 terminates at a rounded atraumatic tip 125.

In this embodiment, the length of the end portion 124 is approximately 5 mm, and it may have other lengths, such as 8 mm, or longer or shorter lengths. The end portion 124 in this embodiment bends downwardly from the general plane of the ventricular winding 112 by an angle of approximately 15 degrees, and it may bend at other angles, such as 25 degrees, or larger or smaller angles. In this embodiment, the design results in a gap in the axial direction between the general plane of the ventricular winding 112 and the tip 125 of the end portion 124 of approximately 1 mm to 5 mm, but larger or smaller gaps are possible.

The grasping element 120 is connected to the center 114 of the ventricular winding 112 and extends upwardly from the center 114 of the ventricular winding 112. As shown in FIG. 1, the grasping element 120 is formed of a continuation of the wire structure of the ventricular winding 112. The wire structure forming the grasping element 120 extends upwardly from the general plane of the ventricular winding 112 at an angle of approximately 90 degrees, although other angles may be used. After extending upwardly from the ventricular winding 112, the wire structure of the grasping element 120 bends at a top bend 121 and extends downwardly to an end 122 of the wire structure, thereby forming a loop. The top bend 121 forms an atraumatic tip, and the end 122 may be blunt or rounded or may form a junction with the adjacent portion of the wire structure, similar to the junction 126. In alternative embodiments, the grasping element 120 may be substantially straight, curved, bent, helical, or any other suitable shape. In one example, the length of the grasping element 120 (from the connection with the ventricular winding 112 to its top at bend 121) may be approximately 5 mm to 20 mm, for example 6 mm to 8 mm or 10 mm, but longer or shorter lengths are possible.

As can be seen in FIG. 1, the implantable heart valve repair device 110 is free of any atrial stabilizing section, i.e., the device does not have any part that is adapted to stabilize the device by engaging tissue on the atrial side of the valve, such as the wall of the atrium or the annulus of the valve on the atrial side. It is possible, for example, that after implantation the grasping element 120 extends through the valve to the atrial side, and it may contact the leaflets as they close. However, neither the grasping element 120 nor any other part of the device 110 is adapted to engage tissue on the atrial side of the valve in a manner that stabilizes or anchors the device with respect to the atrium.

The device 110, including the ventricular winding 112 and the grasping element 120, is comprised of a wire. In alternative embodiments, all or part of the device may comprise a wire, a bundle of wires, a strip, a rod, or a tube, and different sections of the device or parts thereof may comprise a wire, a bundle of wires, a strip, a rod, a tube, or a combination thereof. The structure may be formed by bending or otherwise shaping a wire, a bundle of wires, a strip, a rod, or a tube into the desired shape. The desired shape may be obtained by "baking" the material in a certain shape at a certain temperature such that the material will remember that shape. Alternatively, the shape may be formed as the wire, bundle of wires, strip, rod, or tube is formed. For example, the spiral shape of the ventricular winding may be chemically or laser etched or otherwise cut from a sheet of material, in which case the strip or rod is formed simultaneously with the spiral shape. The device may be formed of more than a single structure or material; for example, a tube with a wire core may form the ventricular winding and/or the grasping element, with the other element formed of a similar or dissimilar structural component.

The use of a bundle of wires can provide the device with high axial strength as well as high flexibility. For example, the use of several thin wires in a twisted bundle or in a braided bundle provides high axial strength and flexibility that can be determined by the twisting or braiding structure.

The wire, bundle of wires, strip, rod or tube may have any suitable cross-sectional shape. For example, the wire, bundle of wires, strip, rod or tube may have a circular, elliptical, square, rectangular, hexagonal, or other cross-sectional shape. The wire, bundle of wires, strip, rod, or tube may have different cross-sectional shapes or sizes at different places along its length. The wire of device 110 has a circular cross-sectional shape along its length. In one example, the wire, bundle of wires, strip, rod, or tube may have a diameter, width or thickness of approximately 0.2-1.0 millimeters (e.g., 0.4 millimeters), but larger or smaller dimensions are possible.

The wire of device 110 is formed from a suitable shape memory metal, for example nitinol. Other suitable materials may be used for all or part of the wire(s), rod(s), or tube(s) of the device, for example other shape memory materials, other metallic materials, plastic materials and/or composite materials.

The device 110 of FIG. 1 has rounded ends 121, 125 at the ends of the grasping element 120 and end portion 124. In alternative embodiments, one or more ends of the wire, bundle of wires, strip, rod, or tube may be rounded, squared-off, or pointed. As described further below, the device may have one or more anti-rotation elements.

As can be seen in FIG. 1, the spiral of ventricular winding 112 can be considered as being wound in a clockwise direction when viewed from the top and starting from the center and moving outward. In an alternative embodiment, the spiral of the ventricular winding 112 can be wound in an opposite direction.

The wire, bundle of wires, strip, rod, or tube may have one or more grooves in its outer surface. The groove in the outer surface of the wire, bundle of wires, strip, rod, or tube may extend around the perimeter of the wire, bundle of wires, strip, rod, or tube and/or in the direction of the length of the wire, bundle of wires, strip, rod, or tube. As one example, the wire, bundle of wires, strip, rod, or tube may have one more grooves that extend in a substantially helical path along the wire, bundle of wires, strip, rod, or tube. Such grooves may serve different purposes. For example, one or more grooves may be used to create different flexibilities at different places of the device, to facilitate ingrowth of tissue, to facilitate grasping and manipulation (e.g., pushing, pulling, turning, etc.) of the device, and/or as channels for drug delivery. For example, a helical groove can be used to facilitate rotation of the device as it is being delivered from or withdrawn into a delivery catheter. Similarly, a helical or other groove can direct cell growth in layers in a preferred direction, thereby reducing scar formation.

The wire, bundle of wires, strip, rod, or tube may have one or more holes in it. The holes may be through-holes extending all the way through the thickness of the wire, bundle of wires, strip, rod, or tube, and/or the holes may be pockets or dimples in the outer surface of the wire, bundle of wires, strip, rod, or tube. The holes may be a series of holes extending along the length and around the periphery of the wire, bundle of wires, strip, rod, or tube. The holes may serve different purposes. For example, one or more holes may be used to create different flexibilities at different places of the device, to facilitate ingrowth of tissue, to facilitate grasping and manipulation of the device, to provide ports for injection of a contrast agent, and/or as sites for drug delivery.

The device may comprise a coating on the wire, bundle of wires, strip, rod, or tube. The coating is preferably a biocompatible coating that may be used, for example, to reduce possible negative reactions from the tissue where the device is implanted, to reduce friction (as a lubricious coating) to assist in delivery of the device, to reduce friction in areas where the device is designed to be moved against tissue (for example, along the path of the spiral of the ventricular winding), to increase friction in areas where it is desired to reduce movement or to anchor the device, to deliver a suitable drug, for radiopacity, to encourage cell and tissue growth that would assist in fixation (e.g., of the upper section), to encourage tissue growth between the chords and/or leaflets, and/or for other purposes. With respect to radiopacity, the entire device or selected points on the device may be coated or plated with a material allowing the physician to understand the location of the device during and/or after the implantation procedure. For example, the ends of the spiral may be plated with a radiopaque material. If selected points on the device are plated, the plating at the selected points may have a certain shape (e.g., a line, arrow, etc.) to assist in understanding the orientation of the device. In another example, in the case of a device formed of a tube, the tube may be coated to ensure that the coated tube is sealed in order that the tube may be used, for example, for pressure measurement. When the coating is a drug-release coating, the coating may comprise a carrier (for example, a polymer) with the drug in the carrier for drug elution over a suitable period of time. The drug eluting mechanism may use a biodegradable carrier (e.g., a biodegradable polymer) or a stable carrier (e.g., a stable polymer) that allows the drug elution through diffusion of drug molecules.

Figure 2:
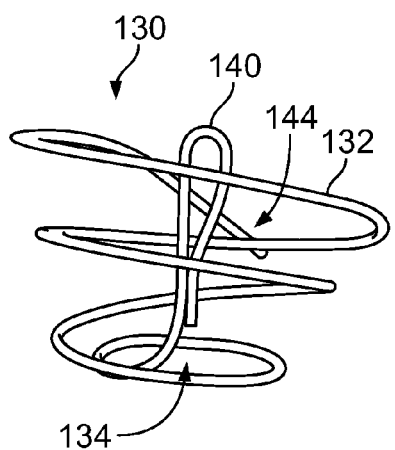
FIG. 2 shows a side view of another embodiment of a heart valve repair device.

FIG. 2 shows another embodiment of a heart valve repair device 130. The device 130 comprises a ventricular winding 132 and a grasping element 140. The ventricular winding 132 has a generally spiral shape, defined by the wire structure of the ventricular winding 132 forming a winding around a center 134 of the ventricular winding 132. The wire structure of the winding emanates from the center 134 and gradually moves away from the center 134 as it winds around the center 134. In the case of device 130, the winding of the ventricular winding 132 moves outward from the center 134 at a generally constant rate, thereby forming a substantially circular shape (in top view), while at the same time the winding moves upward from its starting point at the center 134, thereby forming a substantially conical helix opening upward, with the base of the cone above the vertex. In an alternative embodiment, the winding of the ventricular winding moves outward from its starting point at the center while at the same time moving downward from its starting point at the center, thereby forming a substantially conical helix opening downward, with the base of the cone below the vertex. As shown in FIG. 2, the ventricular winding 132 terminates at its outer periphery at an atraumatic end portion 144, which is bent downwardly, similar to end portion 124.

In the device 130, like the device 110, the winding structure of the ventricular winding 132 forms a path that starts from an opening at the outer periphery of the spiral and that moves toward the center 134 of the spiral as the path winds around the center 134 of the spiral.

The device 130, like the device 110, may be comprised of a wire having a circular cross-section. The wire of device 130 may be formed of a suitable shape memory metal, for example nitinol.

The grasping element 140 of device 130 is similar in construction to the grasping element 120 of device 110. As can be seen in FIG. 2, the device 130 is free of any atrial stabilizing section.

As would be understood by persons of ordinary skill in the art from the above descriptions, alternative embodiments of the device 130 may be formed, using the variations described above with respect to the device 110. Thus, for example, the ventricular winding 132 and the grasping element 140 may comprise other forms, shapes, sizes and/or materials as described above with respect to the device 110. The ends of the device may be rounded, squared-off, or pointed. The device 130 may have one or more anti-rotation elements, as described further below. The ventricular winding 132 and/or the grasping element 140 may have one or more grooves and/or holes, as described above. The device may comprise a coating, as described above.

Figure 3:
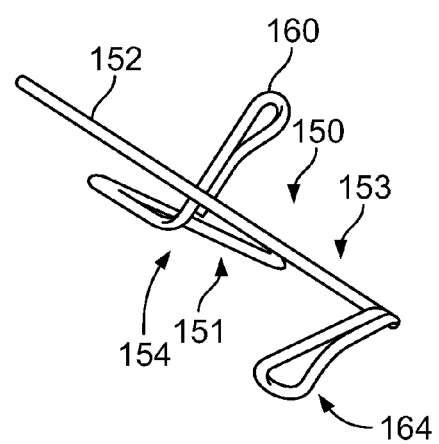
FIG. 3 shows a side view of another embodiment of a heart valve repair device.

FIG. 3 shows another embodiment of a heart valve repair device 150. The device 150 comprises a ventricular winding 152 and a grasping element 160. The ventricular winding 152 has a generally spiral shape, defined by the wire structure of the ventricular winding 152 forming a winding around a center 154 of the ventricular winding 152. The wire structure of the winding emanates from the center 154 and gradually moves away from the center 154 as it winds around the center 154. In the case of device 150, in an inner section 151, the winding of the ventricular winding 152 moves outward from the center 154 at a generally constant rate, thereby forming a substantially circular shape (in top view), while at the same time the winding moves upward from its starting point at the center 154, thereby forming a substantially conical helix opening upward, with the base of the cone above the vertex. Then, the inner section 151 transitions to an outer section 153, in which the winding of the ventricular winding 152 stays substantially in a single plane as it moves outward from the center 154 at a generally constant rate. In an alternative embodiment, the inner section may stay substantially in a single plane with the outer section forming a section of a substantially conical helix. As shown in FIG. 3, the ventricular winding 152 terminates at its outer periphery at an atraumatic end portion 164, which is bent downwardly, similar to end portion 124.

In the device 150, like the device 110, the winding structure of the ventricular winding 152 forms a path that starts from an opening at the outer periphery of the spiral and that moves toward the center 154 of the spiral as the path winds around the center 154 of the spiral.

The device 150, like the device 110, may be comprised of a wire having a circular cross-section. The wire of device 150 may be formed of a suitable shape memory metal, for example nitinol.

The grasping element 160 of device 150 is similar in construction to the grasping element 120 of device 110. As can be seen in FIG. 3, the device 150 is free of any atrial stabilizing section.

As would be understood by persons of ordinary skill in the art from the above descriptions, alternative embodiments of the device 150 may be formed, using the variations described above with respect to the device 110. Thus, for example, the ventricular winding 152 and the grasping element 160 may comprise other forms, shapes, sizes and/or materials as described above with respect to the device 110. The ends of the device may be rounded, squared-off, or pointed. The device 150 may have one or more anti-rotation elements, as described further below. The ventricular winding 152 and/or the grasping element 160 may have one or more grooves and/or holes, as described above. The device may comprise a coating, as described above.

Figure 4:
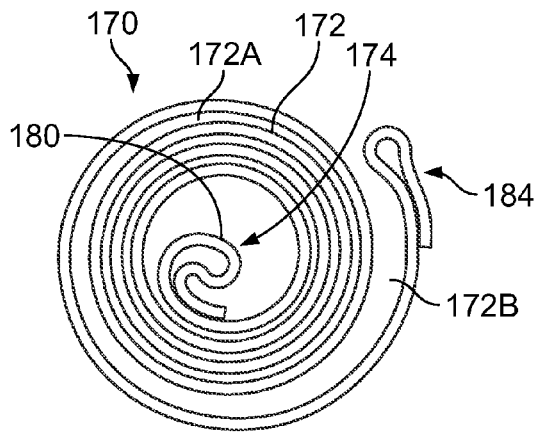
FIG. 4 shows a top view of another embodiment of a heart valve repair device.

FIG. 4 shows another embodiment of a heart valve repair device 170. The device 170 comprises a ventricular winding 172 and a grasping element 180. The ventricular winding 172 has a generally spiral shape, defined by the wire structure of the ventricular winding 172 forming a winding around a center 174 of the ventricular winding 172. The wire structure of the winding emanates from the center 174 and gradually moves away from the center 174 as it winds around the center 174. In the case of device 170, the winding of the ventricular winding 172 moves outward from the center 174 at an uneven rate. Thus, the gap between adjacent turns of the winding is non-constant, as can be seen by a comparison between smaller inner gap 172A and larger outer gap 172B. As shown in FIG. 4, the ventricular winding 172 terminates at its outer periphery at an atraumatic end portion 184.

In the device 170, like the device 110, the winding structure of the ventricular winding 172 forms a path that starts from an opening at the outer periphery of the spiral and that moves toward the center 174 of the spiral as the path winds around the center 174 of the spiral.

The device 170, like the device 110, may be comprised of a wire having a circular cross-section. The wire of device 170 may be formed of a suitable shape memory metal, for example nitinol.

The grasping element 180 of device 170 may be similar in construction to the grasping element 120 of device 110 or may be generally in the same plane as the ventricular winding 172. As can be seen in FIG. 4, the device 170 is free of any atrial stabilizing section.

As would be understood by persons of ordinary skill in the art from the above descriptions, alternative embodiments of the device 170 may be formed, using the variations described above with respect to the device 110. Thus, for example, the ventricular winding 172 and the grasping element 180 may comprise other forms, shapes, sizes and/or materials as described above with respect to the device 110. The ends of the device may be rounded, squared-off, or pointed. The device 170 may have one or more anti-rotation elements, as described further below. The ventricular winding 172 and/or the grasping element 180 may have one or more grooves and/or holes, as described above. The device may comprise a coating, as described above.

As mentioned above, the implantable heart valve repair devices 130, 150, and 170, like the heart valve repair device 110 and other heart valve repair devices described herein, are free of any atrial stabilizing section. Each of the implantable heart valve repair devices 110, 130, 150, and 170 has a stabilizing section that consists only of a ventricular stabilizing section in the form of a ventricular winding 112, 132, 152, and 172, which is adapted to engage tissue only on the ventricular side of the valve and to stabilize the device by the interaction between the ventricular winding 112, 132, 152, and 172 and the chords on the ventricular side of the valve. In some embodiments, these heart valve repair devices also may be described as not having any part that, after implantation, contacts tissue in the atrium or on the atrial side of the valve and/or not having any part that, after implantation, extends into the atrium or on the atrial side of the valve. However, as described above, it is possible in some embodiments for the grasping element to extend through the valve to the atrial side, and it may contact the leaflets. However, these embodiments may be constructed such that neither the grasping element nor any other part of the device is adapted to engage tissue on the atrial side of the valve in a manner that stabilizes or anchors the device with respect to the atrium.

Figure 5A:
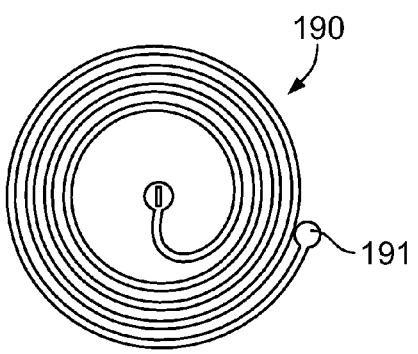
FIGS. 5A-5C show alternative versions of heart valve repair devices with anti-rotation elements.
Figure 5B:
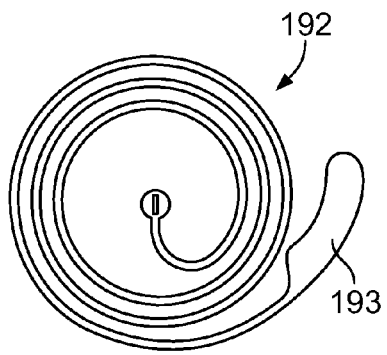
Figure 5C:
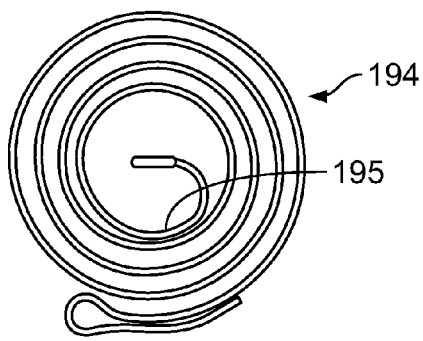

FIGS. 5A-5C illustrate examples of anti-rotation elements that may be used with a heart valve repair device, including any of the heart valve repair devices described herein. FIG. 5A shows a heart valve repair device 190 having an anti-rotation element 191 in the form of a protrusion on the end of the ventricular winding. FIG. 5B shows a heart valve repair device 192 having an anti-rotation element 193 in the form of an enlarged tooth on the end of the ventricular winding. FIG. 5C shows a heart valve repair device 194 having an anti-rotation element 195 in the form of an enlarged area on an inner turn of the winding, coming close to or touching an adjacent turn. The anti-rotation elements can help prevent backward rotation of the device after implantation, by allowing easier rotation of the device in the direction of bringing the chords together than in the opposite direction. Thus, for example, a tooth having a slanted front face (on the side facing the outer opening of the path of the spiral) and steep back face can permit rotation of the device in the direction that brings the leaflets together (by the chords passing over the slanted front face) and can help resist rotation in the opposite direction (by the chords acting against steep back face, thereby resisting backward rotation).

In the example of one or more protrusions 191 as shown in FIG. 5A, the force applied by the delivery system during the process of turning the device 190 to capture the chords can result in the wire structure flexing sufficiently to create a large enough gap between the protrusion 191 and the adjacent turn of the winding in order to allow the chords to pass therethrough, so that the device 190 may be wound around the chords. Similarly, in the example of one or more protrusions 193 as shown in FIG. 5B, the force applied by the delivery system during the process of turning the device 192 to capture the chords can result in the wire structure flexing sufficiently to create a large enough gap between the tooth 193 and the adjacent turn of the winding in order to allow the chords to pass therethrough, so that the device 192 may be wound around the chords. Similarly, in the example of one or more enlarged areas 195 as shown in FIG. 5C, the force applied by the delivery system during the process of turning the device 194 to capture the chords can result in the wire structure flexing sufficiently to create a large enough gap between the enlarged area 195 and the adjacent turn of the winding in order to allow the chords to pass therethrough, so that the device 194 may be wound around the chords. In each of these examples, the geometry of the anti-rotation element(s) helps prevent the device from unintentionally rotating in the opposite direction.

Figure 6:
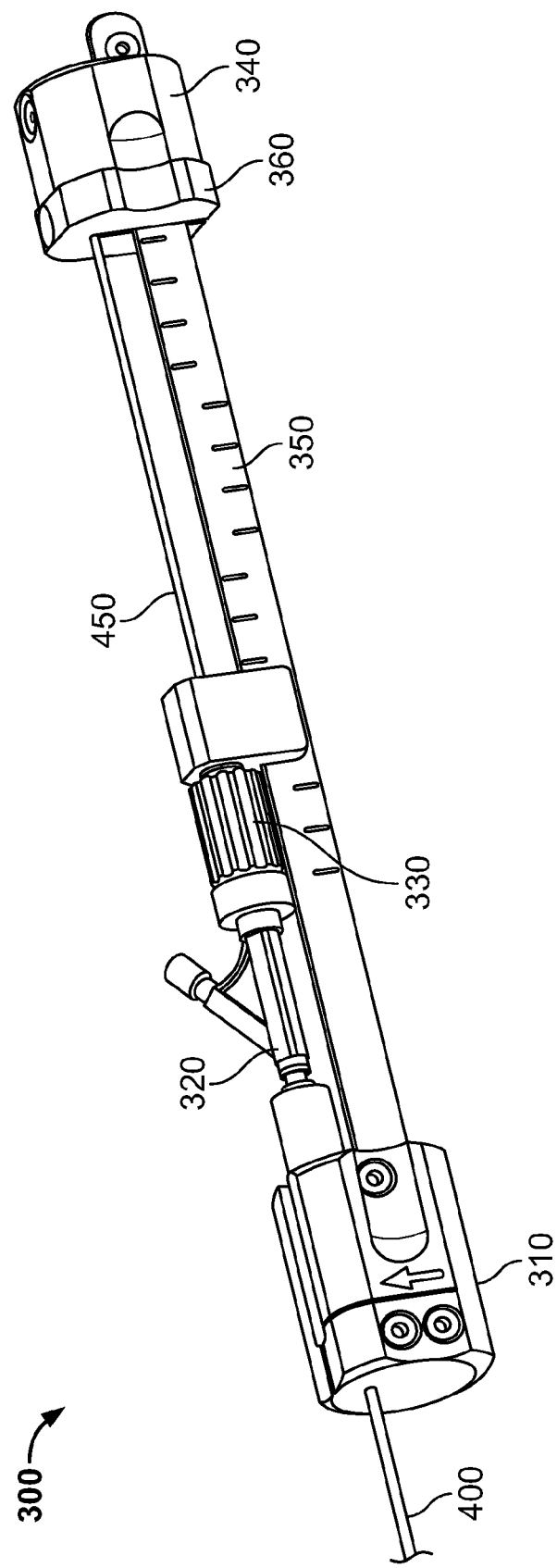
FIG. 6 illustrates a proximal end of a delivery system for implanting a heart valve repair device.

FIG. 6 illustrates a proximal end of a delivery system of a type that may be used for implanting a heart valve repair device, such as any of the heart valve repair devices described herein. The delivery system 300 includes a flexible applicator 400, which is generally tubular in shape, and an internal rod 450, which is moveable within the applicator 400. An applicator gripper 310 may be used to help push, withdraw, and rotate the applicator 400, in both clockwise and counterclockwise directions. An applicator irrigation port 320 allows injecting irrigation fluids into the applicator 400. An internal rod torquer 330 may be used to rotate the internal rod 450 within the applicator 400. An internal rod grip 340 is connected to the internal rod 450 and may be used to control movements of the internal rod 450, including pushing it forward in order to eject a hook that is connected to internal rod 450, as described below. A scale or ruler 350 facilitates measuring how far the internal rod 450 has been advanced, so as to determine the position of the hook inside the applicator 400. A safety plate 360 prevents inadvertent advancement of the internal rod grip 340, in order to eliminate the possibility of accidentally pushing the hook outside of the applicator 400.

Figure 7A:
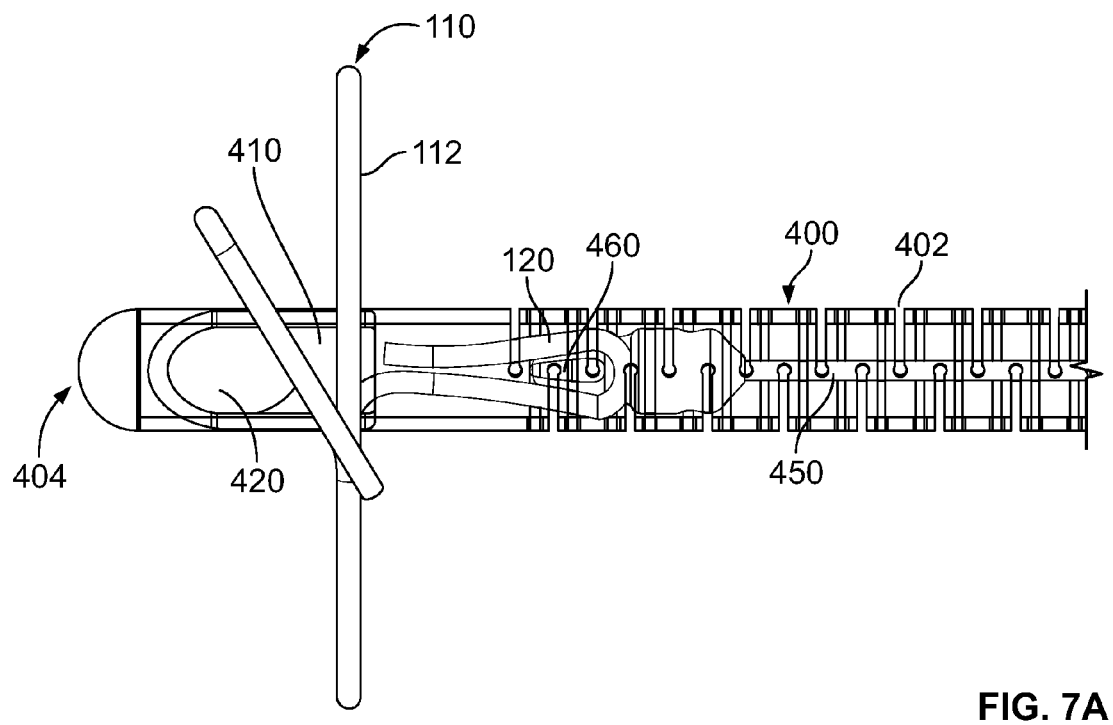
FIG. 7A shows a top view of a distal end of the delivery system of FIG. 6.
Figure 7B:
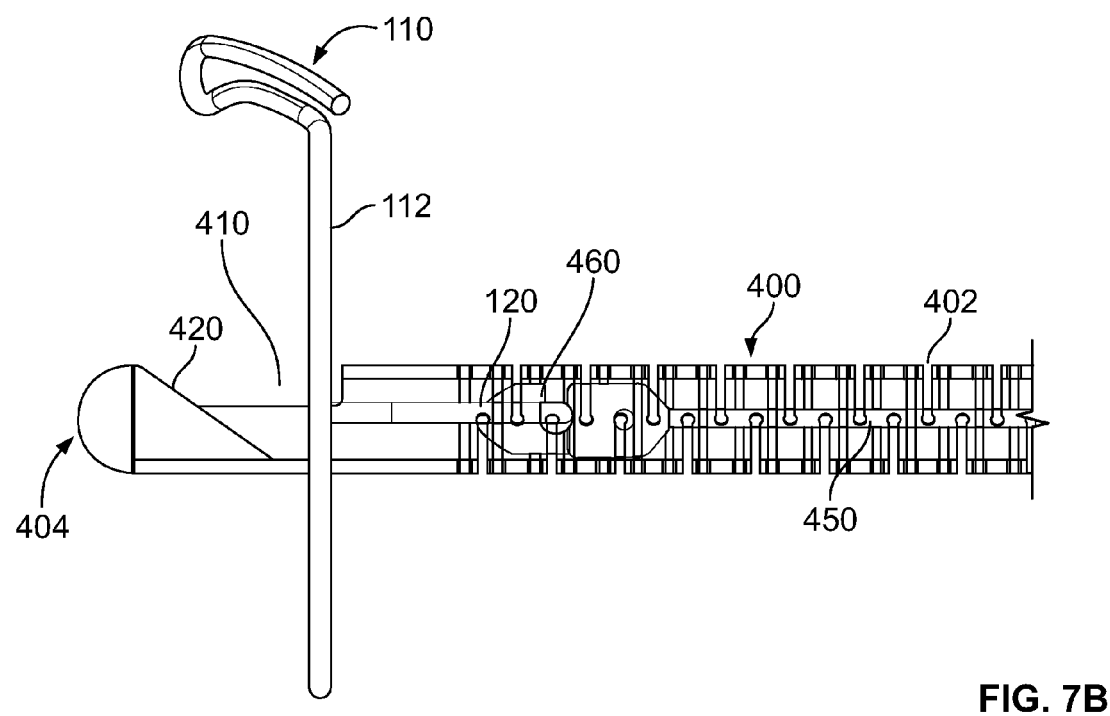
FIG. 7B shows a side view of a distal end of the delivery system of FIG. 6.

FIGS. 7A and 7B show top and side views, respectively, of a distal end of the delivery system 300, with a heart valve repair device 110 loaded on the delivery system 300. In these figures, it can be seen that the flexible applicator 400 has lateral slots 402 to facilitate bending. Other manners of imparting flexibility to a catheter may be used, including selection of appropriate flexible material(s). The applicator 400 has a rounded, atraumatic distal end 404. The applicator 400 has a window 410 through which all or part of the heart valve repair device may be ejected. A ramp surface 420 adjacent the distal end of the window 410 facilitates ejection of the device, as described below.

The internal rod 450 terminates in a hook 460. The hook 460 is designed to hold the grasping element of the heart valve repair device while the hook 460 is inside the applicator 400, proximal to the window 410.

In a first example implantation, the delivery system 300 holds a heart valve repair device 110 as shown in FIGS. 7A and 7B, with the ventricular winding 112 positioned outside of the lumen of the applicator 400 and with the grasping element 120 positioned inside the lumen of the applicator 400 and held by the hook 460. In this position, the internal wall of the lumen of the applicator 400 prevents the grasping element 120 from exiting the hook 460. Thus, as long as the hook 460 is inside the lumen of the applicator 400 (and not in the window 410), the grasping element 120 remains hooked on the internal rod 450 and is thereby locked to the internal rod 450.

The delivery system 300 is used in conjunction with a catheter tube, for example a steerable catheter as is known in the art. One example of a steerable catheter is the AGILIS catheter of St. Jude Medical, Inc. The catheter is sized to accommodate the applicator 400 of the delivery system 300. For example, if the applicator 400 has a size of 7.5 French, the outer catheter may have a size of 12 French. This is just an example, as other sizes may be used.

In this first example, with the ventricular winding 112 positioned outside of the lumen of the applicator 400, the distal end of the applicator 400 is advanced into the proximal end of the steerable catheter. Because the lumen of the steerable catheter is only slightly larger than the outer diameter of the applicator 400, and smaller than the outer periphery of the ventricular winding 112, as the applicator 400 is further advanced into the catheter, an internal turn of the ventricular winding 112 comes into contact with the edge of the catheter tube at its proximal end. Further advancement of the applicator 400 into the catheter will thereby cause the ventricular winding 112 to unwind and straighten as it is advanced into the catheter along with the applicator 400. It will be appreciated that the center part of the ventricular winding 112 will be advanced into the catheter first, and the ventricular winding 112 will unwind from the center to the outer periphery as the ventricular winding 112 is advanced into the catheter. When fully advanced into the catheter, the generally unwound ventricular winding 112 is held in a relatively straightened position between the outer wall of the applicator 400 and the inner wall of the catheter lumen. The applicator 400 may be advanced into the catheter either before or after the catheter is tracked to the patient's heart.

The catheter is positioned adjacent the heart valve to be treated, for example a mitral valve, by a method known in the art. The approach may be, for example, a transeptal approach, with the catheter entering the left atrium through the septum between the right atrium and the left atrium. To facilitate a transeptal approach, the delivery system may include an atrial septum dilator. Other approaches alternatively may be used, including, for example, a transfemoral approach through the femoral artery and through the aorta and into the left ventricle, a transapical approach through the heart wall at the heart apex into the left ventricle, or a transatrial approach through the heart wall into the left atrium. Similarly, when the valve to be treated is the tricuspid valve, the catheter is positioned adjacent the valve by a method known in the art (such as being introduced to the heart via a jugular vein or the vena cava).

Once the guide catheter is adjacent the heart valve, the tip of the guide catheter may be moved and/or turned so that it is facing the heart valve leaflets. The applicator 400 then may be advanced relative to the catheter, thereby ejecting the ventricular winding 112 from the catheter. Because of the shape memory of the ventricular winding 112, the heart valve repair device 110 returns to a position as shown in FIGS. 7A and 7B, inside the heart. The ejection of the ventricular winding 112 from the catheter may be performed in the atrium. Alternatively, the ejection of the ventricular winding 112 from the catheter may be performed in the ventricle. If ejected in the atrium, the delivery system 300 then may be used to advance the distal end of the applicator 400, and with it the ventricular winding 112, into the ventricle. The distal end of the applicator 400 and the ventricular winding 112 may be pushed through the valve into the ventricle.

Figure 8:
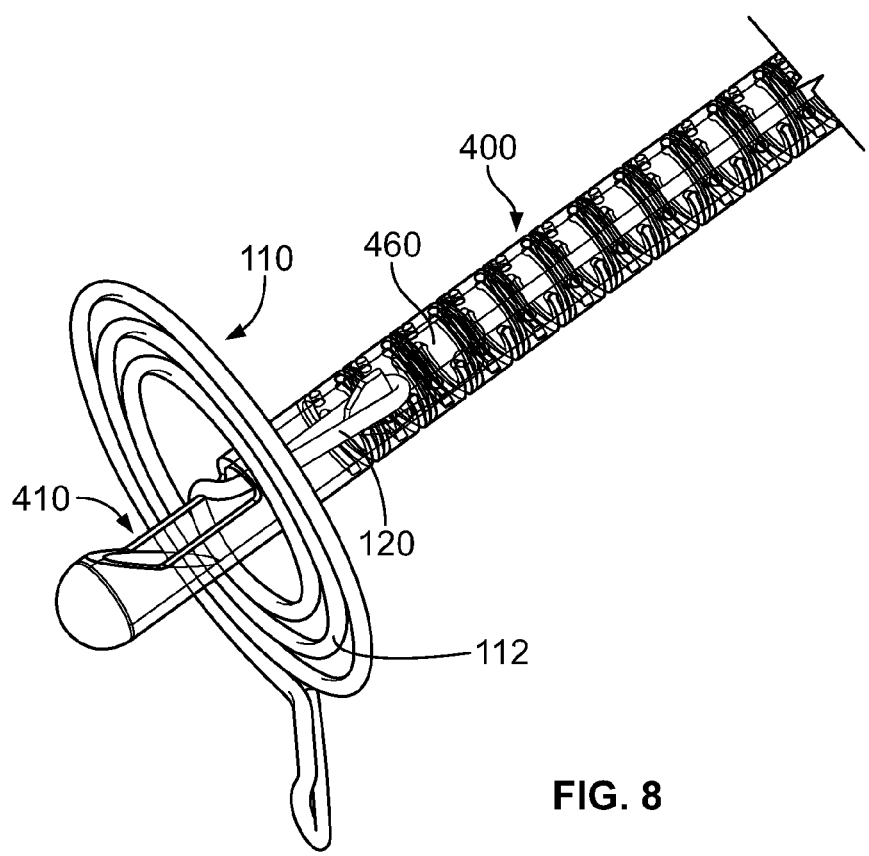
FIG. 8 shows a perspective view of the distal end of the delivery system of FIG. 6 with a heart valve repair device being held by the delivery system.

FIG. 8 shows a perspective view of the distal end of the delivery system 300, with the ventricular winding 112 ejected from the guide catheter and outside of the tube of the applicator 400, and with the grasping element 120 still inside the tube of the applicator 400 and connected to the hook 460. In this position, rotation of the applicator 400 causes the heart valve repair device 110 to be rotated along with it. During rotation of the applicator 400, the action of the frame of the window 410 against the device 110 causes the device 110 to rotate with the applicator 400. Additionally or alternatively, the hook 460 or another part of the delivery system 300 may sufficiently hold the device 110 to cause the device 110 to rotate. Due to the geometry of the device, the axis of the delivery system can be generally aligned with the axis of rotation of the ventricular winding.

In the condition as shown in FIG. 8, and with the ventricular winding 112 positioned in the ventricle, the delivery system may be used to capture the desired chords with the ventricular winding 112. The physician may maneuver the ventricular winding 112 from side to side to capture specific chords in order to bring desired areas of the leaflets together. For example, by suitably moving and turning the ventricular winding 112, the chords associated with the leaflet areas A1 and P1 (FIG. 12) may be captured. Additionally or alternatively, the chords associated with the leaflet areas A2 and P2 and/or A3 and P3 (FIG. 12) may be captured.

In this manner, the desired chords associated with the anterior papillary muscle and the desired chords associated with the posterior papillary muscle are positioned within the path 118 of the generally spiral shape of the ventricular winding 112. By turning the ventricular winding 112, whether by turning the applicator 400 or by another suitable mechanism, the ventricular winding 112 is thereby turned to wind around the selected anterior and posterior chords. As the ventricular winding 112 is turned, the spiral shape forces the chords within the path 118 closer to the center 114 of the ventricular winding 112. In this manner, the captured anterior chords and posterior chords are forced closer together, thereby reducing a gap between the selected chords associated with the anterior papillary muscle and the selected chords associated with the posterior papillary muscle. By doing this, because the selected chords are attached to the selected areas of the leaflets, the selected areas of the leaflets are brought closer together.

In order that the ventricular winding may be turned to move the chords in this manner and may hold the chords, the heart valve repair device, or at least the ventricular winding, should have sufficient stiffness such that the spiral shape is generally maintained. Thus, the device should be sufficiently rigid so as to maintain the spiral shape on its own and under the forces applied to it by the chords.

In alternative embodiments in which the ventricular winding comprises more than one spiral, the device may be formed so that it can gather and move the chords with fewer rotations. Thus, for example, with the ventricular winding comprising multiple spirals and with the openings for the spirals positioned at different places around the perimeter of the ventricular winding, chords at different places around the perimeter of the ventricular winding may be gathered simultaneously and moved toward the center simultaneously.

In order to adjust the device, after the physician has turned the ventricular winding 112 in a first direction as described above, the physician may turn the ventricular winding 112 back in the opposite direction in order to allow the chords to move apart by some amount. Thus, in this example, after the positioning resulting from clockwise turning, the physician may turn the ventricular winding 112 counterclockwise (when viewed from the top) in order to allow the captured chords to move away from the center 114 of the ventricular winding 112, thereby allowing them to separate by some distance. The physician can monitor the positioning of the chords and leaflets and turn the ventricular winding 112 clockwise or counterclockwise as needed in order to obtain the desired result.

If desired, after the ventricular winding 112 has been rotated into the desired rotational position, the physician may pull the ventricular winding 112 to bring it closer to the heart valve. This may be accomplished by retracting the applicator 400.

Figure 9:
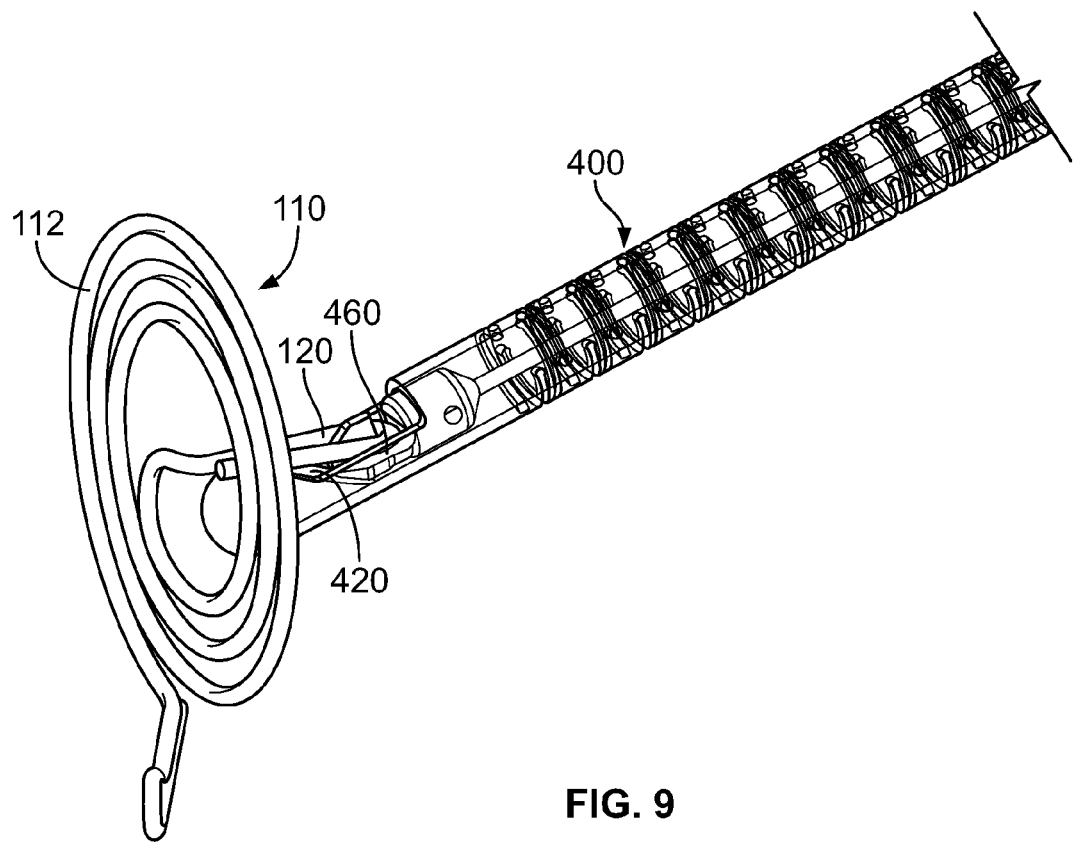
FIG. 9 shows a perspective view of the distal end of the delivery system of FIG. 6 with a heart valve repair device being ejected from the delivery system.

When the ventricular winding 112 is in the desired position, the remainder of the device 110 is ejected from the applicator 400, as shown in FIG. 9. With the applicator 400 held relatively stable, the internal rod 450 is advanced distally within the applicator 400. This moves the hook 460 to be located at the window 410. During this distal advancement, the grasping element 120 is advanced distally against the ramp surface 420, which forces the grasping element 120 away from the applicator 400 and the hook 460. With the hook 460 in the window 410, the grasping element 120 is no longer prevented from exiting the hook 460 by the internal wall of the lumen of the applicator 400. The grasping element 120 is released from the hook 460, and the device 110 is left in place. The delivery device 300 is then withdrawn from the patient. This leaves the heart valve repair device 110 implanted in the patient.

If the procedure is one in which the valve is approached from the atrium as described above, once the device is implanted in the ventricle, the grasping element will be pointing generally toward the atrium. If, on the other hand, the procedure is one in which the valve is approached from the ventricle, once the device is implanted in the ventricle, the grasping element will be pointing generally away from the atrium and generally toward the apex of the heart.

Other heart valve repair devices as described herein, such as the heart valve repair devices 130, 150, 170, and 190, and the variations described above with respect to the heart valve repair devices 110, 130, 150, 170, and 190, may be implanted in a similar manner as described above.

The inventive heart valve repair devices as described herein provide certain advantages with respect to prior devices. As discussed above, in prior heart valve repair devices for capturing leaflet chords as exemplified in certain prior devices, the devices have included parts or sections for anchoring the devices relative to the atrium, in order to ensure that the devices remained stable in the heart after implantation. By contrast, the inventive heart valve repair devices 110, 130, 150, 170, and 190, and the variations described above with respect to these devices, depart from these prior teachings and are free of any atrial stabilizing section. The inventors have found that not only is it possible to implant the inventive heart valve repair devices and have them remain stable in the heart after implantation despite the absence of any atrial stabilizing section, but the inventors also have found that the inventive heart valve repair devices provide previously unrecognized advantages that could not be attained by prior devices that were anchored to the atrium.

As the heart pumps, the various parts of the heart are in motion. The chords connecting the papillary muscles to the leaflets are in motion. A heart valve repair device as described herein without any atrial stabilizing section is free to move along with the chords, while at the same time retaining the chords in their drawn-in condition for leaflet coaptation. Over time, tissue may grow around the ventricular winding such that the ventricular winding becomes substantially embedded in the chords. This tissue enveloping of the device results in a fixation of the device to the chords.

In prior devices that have included atrial stabilizing sections, the devices have been anchored relative to the atrium. However, during the beating of the heart and the opening and closing of the valves, the chords move relative to the atrium. Thus, when such a prior device is implanted and anchored to the atrium, the chord movement relative to the atrium results in chord movement relative to the device. A device anchored to the atrium is constrained from moving freely with the chords. This constraint can occur at the time of the implantation procedure and longer. When a device is constrained in this manner, the chords can rub relative to such a device, which can cause irritation, injury, and/or rupture of the chords.

By contrast, a heart valve repair device as described herein, without any atrial stabilizing section, can be affixed only to the chords. Thus, the device is free to move along with the chords, such as in an up-and-down direction generally in the direction of the axis of implantation, while at the same time maintaining the chords in their drawn-in condition for leaflet coaptation. This movement of the device can occur relative to the atrium. Thus, by being free of any atrial stabilizing section, the device has the previously unrealized advantages of reducing or eliminating the potential for chord movement relative to the device and reducing or eliminating the consequent potential for irritation, injury, and/or rupture of the chords that can be caused by such relative movement.

While prior devices as discussed above have included atrial anchoring in order to ensure stability after implantation, the inventors have found that a device as described herein, in both ex vivo testing and in vivo animal testing, is stable in the heart after implantation, despite not having an atrial stabilizing section. The device is sufficiently held in place by the interaction between the ventricular winding and the chords. Accordingly, the inventors have found that it is possible to realize the advantages as described herein and have the device be stable in the heart after implantation, without the need for a connected atrial stabilizing section as in the prior devices discussed above.

The use of a device without any atrial stabilizing section can have several additional advantages. For example, by not having an atrial stabilizing section, the device can be smaller, simpler and less expensive to manufacture, easier to implant, more maneuverable to facilitate targeted treatment, less prone to tissue injury, and may improve overall outcome.

The presence of an atrial stabilizing section can result in a relatively larger or longer device, requiring positioning the device on the atrial side as well as on the ventricular side of the valve. Thus, the device without any atrial stabilizing section can lead to easier implantation. Implantation is also facilitated because the device is easier to visualize without any atrial stabilizing section.

Without an atrial stabilizing section, it can be easier to maneuver the relatively small ventricular winding to capture specific groups of chords. The presence of an atrial stabilizing section can limit the range of placement of the device. That is, a relatively large atrial stabilizing section can limit the side-to-side range of the device, potentially limiting the areas in which the device can be placed, and limiting the groups of chords that can be captured. By contrast, the smaller, more maneuverable device leads to an improved ability to address specific chords and/or specific areas of a valve.

The device without an atrial stabilizing section also reduces the chance of tissue injury on the atrial side of the valve, which can occur due to the engagement of tissue on the atrial side. Such engagement can occur during the delivery procedure or after implantation.

A person of ordinary skill in the art will understand that the various heart valve repair devices described herein may be implanted according to the method described above. Various features of the device can facilitate the procedure and functioning.

For example, the grasping element allows the device to be held by the delivery system, so that it can be held, maneuvered, turned, and released as described above. Because the grasping element can extend from at or near the center of the ventricular winding, the device can be turned by simply rotating the ventricular winding generally around the axis of the grasping element. When the device is fully deployed, the grasping element may be located fully within the ventricle or may extend into the atrium.

The end portion of the ventricular winding, bent away from the general plane of the winding, can facilitate capturing of the chords. The distance of the end portion away from the general plane of the winding can determine the span of the potential chords to be grasped. The rounded atraumatic tip of the end portion can help prevent injury to the chords, leaflets, and/or other tissue.

When all or part of the ventricular winding is out of plane, such as in a conical or partially-conical embodiment as shown in FIGS. 2 and 3, the height dimension of the ventricular winding can help maintain the vertical positioning of the device within the ventricle. The height dimension also allows more contact with the chords in the vertical direction. This can reduce the friction between the device and the chords and can increase tissue coverage of the device. In addition, the height dimension can allow easier visualization of the device.

When the spacing of the turns of the ventricular winding is larger toward the outer periphery, as shown in FIG. 4, the design can facilitate capturing the chords (by the larger outer spacing) while also bringing them close together (by the narrower inner spacing).

The device can have anti-rotation elements that can help prevent the ventricular winding from turning backward (in the loosening direction) after implantation. Thus, the ventricular winding can have one or more anti-rotation elements 191, 193, 195, as shown in FIGS. 5A-5C, that help keep the device in place. Other mechanisms for resisting unwinding include the use of different shapes. For example, if the ventricular spiral is in an elliptical shape, the chords will tend to gather in the apices of the long axis of the ellipse. In order for the device to rotate, the chords would need to be drawn closer together, which is a movement they would tend to resist. Accordingly, such an elliptical shape can assist in preventing an unwanted rotation of the device.

It will be appreciated that in procedures in which the delivery system approaches the heart valve from the ventricular side (e.g., in transfemoral and transapical approaches), similar methods to those described above may be used, modified to account for the fact that the delivery system approaches the valve from the opposite side.

Figure 10:
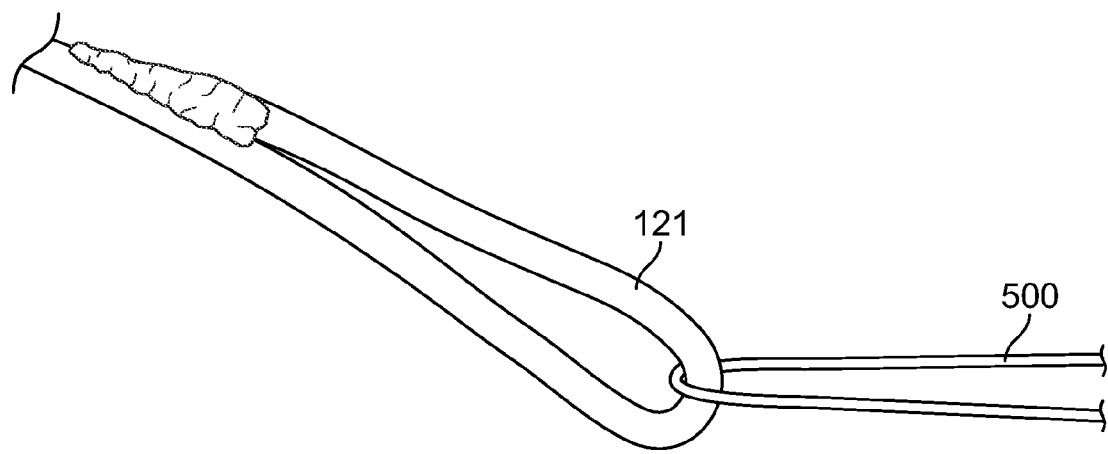
FIG. 10 shows a retention wire threaded through a grasping element of a heart valve repair device.

The delivery system may have means for retrieving and/or moving the heart valve repair device after it has been partially or fully deployed. For example, FIG. 10 shows a retraction wire 500 that may be placed inside the grasping element 121 of the heart valve repair device. The refraction wire 500 can be located inside the applicator 400, but can also remain inside the grasping element 121 after the heart valve repair device has been ejected from the applicator 400. Pulling the refraction wire 500 can withdraw the heart valve repair device back, so that it can be moved to a different position or fully removed from the patient.

Figure 11:
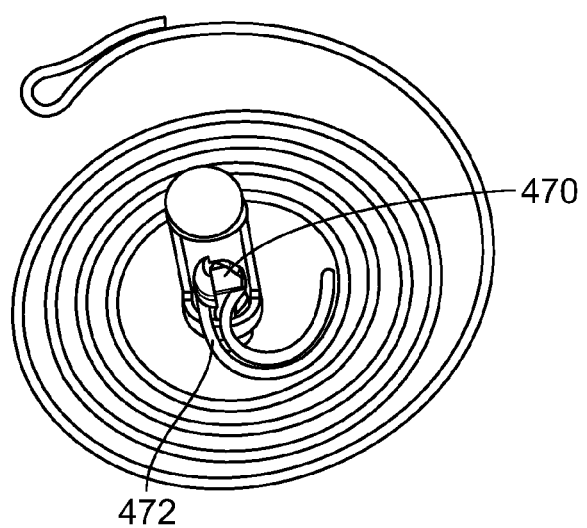
FIG. 11 shows another embodiment of a delivery system hook and grasping element.

FIG. 11 illustrates an alternate form of a hook 470 used to engage a relatively flat grasping element 472. As can be seen, in this embodiment the grasping element 472 is generally in the same plane as the ventricular winding. In this embodiment, the device is released simply by turning the hook 470 relative to the grasping element 472, such that the hook 470 can be withdrawn from the grasping element 472.

While the above method has been described with respect to a device in which the ventricular winding is positioned outside of the applicator for delivery, as in FIG. 8, variations are possible. For example, the ventricular winding may be positioned inside of the applicator 400, whereby it is held in a relatively straightened position. For deployment, the device is ejected from the applicator, at which time the ventricular winding resumes its spiral shape.

As would be understood from the above descriptions by persons of ordinary skill in the art, alternative embodiments of the devices 110, 130, 150, 170, and/or 190 may be implanted generally as described above. The method of implantation may be varied as appropriate with respect to the particular embodiment used and the particular patient being treated.

When a device as described is placed in position as described, the spiral of the ventricular winding reduces a gap between selected chords associated with the anterior papillary muscle and selected chords associated with the posterior papillary muscle. In this manner, the selected areas of the leaflets of the valve are drawn closer together. In some instances, the control of the chords also can reduce the movement of the leaflets, in order to help prevent prolapse. The control of the chords and the drawing of the leaflets closer together facilitate coaptation of the leaflets, such that they can close together sufficiently to correct the regurgitation issue. The device can be left in place as a long-term treatment.

Figure 12:
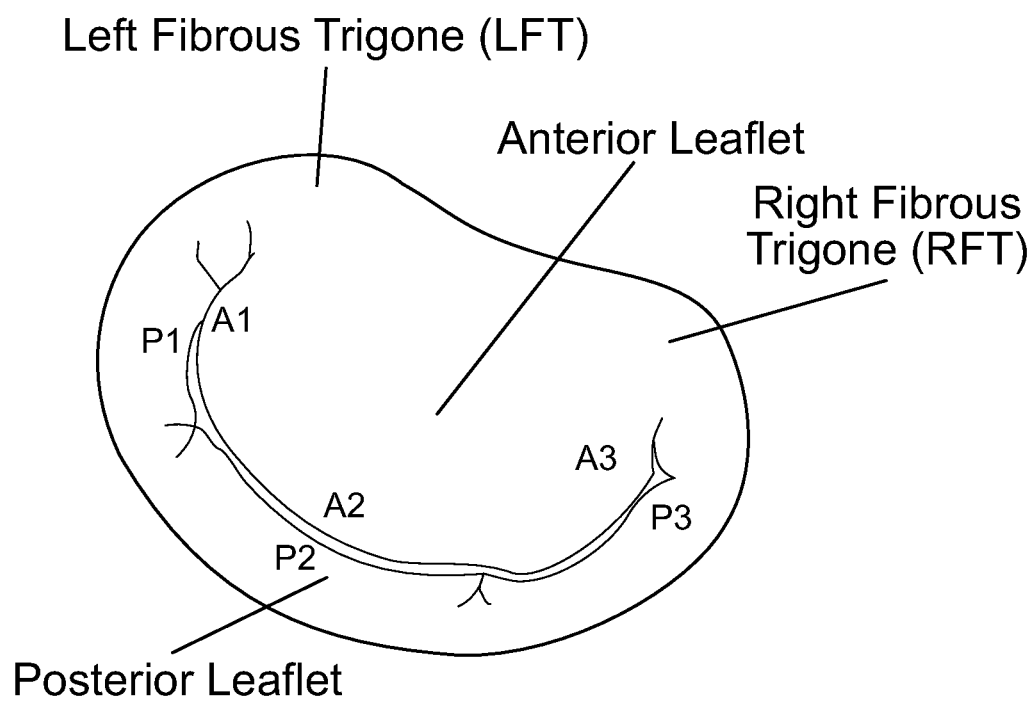
FIG. 12 shows a top view diagram of leaflets of a mitral valve.

FIG. 12 shows a top view of leaflets of a mitral valve. A device as described herein may be used in various positions and for gathering various chords. For example, the device may be positioned approximately in the area of A2 and P2 near the center of the anterior and posterior leaflets. The chords on A2 and P2 are trapped and gathered by the spiral(s) of the ventricular winding. A rotation of the spiral would eventually bring all such chords to the same location, which is the spiral center. In this situation, the gap between A2 and P2 could be brought to zero. Rotating the spiral a little less would result in a narrow gap. The device alternatively may be positioned approximately in the area of A1 and P1, in which case the chords on A1 and P1 are trapped and gathered by the spiral(s) of the ventricular winding, reducing the distance between A1 and P1. The device alternatively may be positioned approximately in the area of A3 and P3, in which case the chords on A3 and P3 are trapped and gathered by the spiral(s) of the ventricular winding, reducing the distance between A3 and P3. A device with a large spiral positioned approximately in the area of A2 and P2 may trap and gather chords on A2, P2, A1, P1, A3 and/or P3, and can be used to reduce the distance between P1 and P3, for example, or A1 and A3.

With a relatively small heart valve repair device as described herein, for example having a ventricular winding with an outside diameter of 1.0-2.0 centimeters, for example, it is possible to capture less than substantially all of the chords and to capture small groups of chords. Implanting such a device may involve positioning the spiral of the ventricular winding between chords rather than around substantially all of the chords. Also, with a relatively small heart valve repair device as described herein, it is possible to implant multiple devices, capturing different sets of chords. The flow through the valve can be adjusted by selectively adjusting the different devices. For example, one device could be placed capturing the chords on A1 and P1, a second device could be placed capturing the chords on A2 and P2, and a third device could be placed capturing the chords on A3 and P3. The flow can be evaluated, and if necessary, adjusted. For example, the device at A1 and P1 could be rotated to bring the associated chords closer together, while the device at A3 and P3 could be rotated in an opposite direction.

In some instances, it may be desired to use the device to draw the leaflets closer and then position a clip anchored to both leaflets or stitch or suture the leaflets together. Thus, the device in conjunction with one or more clips, stitches or sutures can facilitate coaptation of the leaflets.

If desired, the device may be adjusted or withdrawn at a later time, either shortly or long after the implantation. A catheter may be used to access the device. To adjust the device, the physician may turn the spiral of the ventricular winding as described above (e.g., by turning the device) in order to bring the chords closer together or to allow them to separate further apart, as desired. Thus, the turning may be done while performing the initial implantation procedure and/or as an additional later procedure that is separate from the implantation procedure. In this manner, the regurgitation grade can be controlled. Alternatively, if it is desired to withdraw the device altogether, a grasping mechanism may be used to grasp the device and pull it back into the catheter, in essentially the reverse of the procedure that was used to deliver the device.

Numerous alternatives are possible within the scope of the invention. For example, as mentioned above, the winding of the spiral may move away from the center at a non-constant rate. Thus, the spiral density need not be constant.

If the device is formed as a tube, a wire or stiffening element may be placed into the tube in order to change the stiffness and/or shape of the tube or a section of it. For example, a stiffening element may be used to maintain the device in a first shape for delivery (e.g., relatively straight), and the stiffening element may be withdrawn upon delivery of the device from the delivery catheter in order to allow the device to take its implantation shape. In another example, an inner wire may be attached to the distal end of the tube, and the inner wire may be pulled relative to the tube to change the shape of the tube. Pulling the inner wire applies a compressive force to the tube. The tube may be formed with pre-shaped side cuts along the tube, such that it bends in a predetermined pattern, e.g., a spiral pattern, when such a load is applied. A locking mechanism may be used to lock the wire in its loaded position relative to the tube. Different depths and widths of the side cuts and the distance between the side cuts would determine the final shape of the tube element once a load is applied.

The device may have other elements to monitor the functioning of the device and the heart valve. For example, the device may be equipped with a sensor attached to the device. The sensor may be, for example, a pressure sensor, a temperature sensor, and/or a velocity sensor. In this way, the operation of the valve and the blood flow can be monitored. Similarly, the device itself when formed as a tube can be used as a "pig tail" for measuring pressure during or after the implantation procedure.

In one example of the use of sensors, the use of MEMS (microelectromechanical systems) sensors on the device may assist in the implantation procedure or during the years after it. Such sensors may monitor temperature, oxygen saturation, pressure, blood velocity or similar physical characteristics. During the implantation procedure, it is possible to use an xyz (positioning) sensor on the device to assist in the accurate location and positioning of the device by using an external system that reads the information transmitted from the sensor.

Sensor(s) on the device or delivery system may be part of a closed-loop system that uses the signals from the sensor(s) as feedback for automatic delivery and positioning. By using pressure sensors in the ventricle and atrium, the pressure can be continuously monitored as the device is automatically adjusted. The adjustments and monitoring can be continued until target pressure readings are achieved. This automatic positioning with the use of feedback can eliminate the need for manual monitoring and positioning that can be complicated and less accurate.

The device may also have an energy-producing element that produces energy by the flow of blood around the device and/or by the pressure changes using a converter (such as piezoelectric element that is capable of converting mechanical pulse into electric current). The energy may charge a battery that, for example, can be used to transmit signals from one or more sensors as described above.

From the description herein, a person of ordinary skill in the art can recognize that certain embodiments of devices and methods disclosed herein can have several advantages. For example, the device can safely hold the chords without requiring grasping of the leaflets. The movement of the chords toward each other can be controlled by the structure of the device, including, for example, the number of turns of the spiral of the ventricular winding, the radii of those turns, and their shape.

Based on the above description and the accompanying drawings, the principles and operation of the invention, as well as how to make and use the invention, can be understood by persons of ordinary skill in the art. Many embodiments and variations are possible that take advantage of the principles and operation of the invention described herein. The examples described herein and shown in the accompanying drawings are meant as examples only and are not intended to be limiting of the scope of the invention defined by the appended claims.

What is claimed is:

1. The method of repairing a heart valve comprising:
    using a delivery system comprising an applicator tube and an internal rod within the applicator tube to deliver a heart valve repair device to an area of the heart valve, the heart valve repair device comprising a ventricular winding that in an unconstrained condition has a generally spiral shape that moves increasingly further away from a center of the ventricular winding as it winds around the center of the ventricular winding, the generally spiral shape comprising at least a first turn and a second turn wherein at least the first turn is a full turn extending 360 degrees around the center of the ventricular winding, the heart valve repair device further comprising a grasping element that is connected to the center of the ventricular winding and that extends from the center of the ventricular winding, the applicator tube having a window through which at least a part of the heart valve repair device may be ejected, the delivery system comprising a ramp surface adjacent a distal end of the window, the internal rod of the delivery system terminating in a hook adapted to hold the grasping element of the heart valve repair device within the applicator tube, wherein the heart valve repair device is advanced to the area of the heart valve with the ventricular winding held in a constrained condition in which it has a relatively straightened shape;
    releasing the ventricular winding on an atrial side or a ventricular side of the heart valve, thereby allowing the ventricular winding to assume its unconstrained condition in which it has the generally spiral shape;
    after releasing the ventricular winding, positioning the ventricular winding on the ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together; and
    releasing the heart valve repair device from the delivery system by advancing the internal rod distally within the applicator tube, thereby moving the hook distally relative to the applicator tube to be located at the window and advancing the grasping element of the heart valve repair device distally against the ramp surface, which results in forcing the grasping element of the heart valve repair device away from the hook and releasing the grasping element of the heart valve repair device from the hook;
    wherein the heart valve repair device is free of any atrial stabilizing section.

2. The method as in claim 1, wherein the heart valve repair device, including the ventricular winding, comprises a wire, bundle of wires, strip, rod, tube, or a combination thereof.

3. A method as in claim 1, wherein the heart valve repair device is comprised at least in part of a metallic material.

4. The method as in claim 1, wherein the heart valve repair device is comprised at least in part of a shape memory metal material.

5. The method as in claim 1, wherein the heart valve repair device is comprised at least in part of a plastic material.

6. The method as in claim 1, wherein the heart valve repair device is comprised at least in part of a composite material.

7. The method as in claim 1, wherein the heart valve repair device further comprises at least one anti-rotation element.

8. The method as in claim 1, wherein the ventricular winding has an end portion that is angled downwardly.

9. The method as in claim 1, wherein the first leaflet comprises an anterior leaflet of a mitral valve and the second leaflet comprises a posterior leaflet of the mitral valve.

10. The method as in claim 1, wherein the method comprises, after turning the ventricular winding in the first direction, turning the ventricular winding in a second direction such that the captured chords of the first and the second leaflets move further from the center of the ventricular winding, to adjust a positioning of the chords in the device.

11. The method as in claim 1, wherein the steps of positioning the ventricular winding on the ventricular side of the heart valve and turning the ventricular winding in the first direction comprises using the delivery system to turn the ventricular winding in the first direction such that the captured chords of the first and the second leaflets move closer to the center of the ventricular winding.

12. The method of repairing a heart valve comprising:
    delivering a heart valve repair device to an area of the heart valve using a delivery system comprising an applicator tube and an internal rod within the applicator tube, the heart valve repair device comprising a ventricular winding that in an unconstrained condition has a generally spiral shape that moves increasingly further away from the center of the ventricular winding as it winds around a center of the ventricular winding, the generally spiral shape comprising at least a first turn and a second turn wherein at least the first turn is a full turn extending 360 degrees around the center of the ventricular winding, the heart valve repair device further comprising a grasping element that is connected to the center of the ventricular winding and that extends from the center of the ventricular winding, the applicator tube having a window through which at least a part of the heart valve repair device may be ejected, the delivery system comprising a ramp surface adjacent a distal end of the window, the internal rod of the delivery system terminating in a hook adapted to hold the grasping element of the heart valve repair device within the applicator tube;

releasing the ventricular winding thereby allowing the ventricular winding to assume its unconstrained condition in which it has the generally spiral shape;

after releasing the ventricular winding, positioning the ventricular winding on a ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together; and releasing the heart valve repair device from the delivery system by advancing the internal rod distally within the applicator tube, thereby moving the hook distally relative to the applicator tube to be located at the window and advancing the grasping element of the heart valve repair device distally against the ramp surface, which results in forcing the grasping element of the heart valve repair device away from the hook and releasing the grasping element of the heart valve repair device from the hook;

wherein the heart valve repair device does not have any part that extends into an atrial side of the valve after implantation and completion of the method.

13. The method of repairing a heart valve comprising:

delivering a heart valve repair device to an area of the heart valve using a delivery system comprising an applicator tube and an internal rod within the applicator tube, the heart valve repair device comprising a ventricular winding that in an unconstrained condition has a generally spiral shape that moves increasingly further away from the center of the ventricular winding as it winds around a center of the ventricular winding, the generally spiral shape comprising at least a first turn and a second turn wherein at least the first turn is a full turn extending 360 degrees around the center of the ventricular winding, wherein an overall diameter of the ventricular winding is smaller than a diameter of an annulus of the heart valve, the heart valve repair device further comprising a grasping element that is connected to the center of the ventricular winding and that extends from the center of the ventricular winding, the applicator tube having a window through which at least a part of the heart valve repair device may be ejected, the delivery system comprising a ramp surface adjacent a distal end of the window, the internal rod of the delivery system terminating in a hook adapted to hold the grasping element of the heart valve repair device within the applicator tube;

releasing the ventricular winding thereby allowing the ventricular winding to assume its unconstrained condition in which it has the generally spiral shape;

after releasing the ventricular winding, positioning the ventricular winding on a ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together, wherein the ventricular winding captures less than all of the chords associated with the heart valve; and releasing the heart valve repair device from the delivery system by advancing the internal rod distally within the applicator tube, thereby moving the hook distally relative to the applicator tube to be located at the window and advancing the grasping element of the heart valve repair device distally against the ramp surface, which results in forcing the grasping element of the heart valve repair device away from the hook and releasing the grasping element of the heart valve repair device from the hook;

wherein the heart valve repair device is free of any atrial stabilizing section.

14. The method of repairing a heart valve comprising:

using a delivery system comprising an applicator tube and an internal rod within the applicator tube to deliver a heart valve repair device to an area of the heart valve, the heart valve repair device comprising a ventricular winding that in an unconstrained condition has a generally spiral shape, the generally spiral shape comprising at least a first turn and a second turn wherein at least the first turn is a full turn extending 360 degrees around the center of the ventricular winding, wherein in a radial direction from the center of the ventricular winding the second turn is farther away from a center of the ventricular winding than the first turn, the heart valve repair device further comprising a grasping element that is connected to the center of the ventricular winding and that extends from the center of the ventricular winding, the grasping element having an axis, the internal rod of the delivery system terminating in a hook adapted to hold the grasping element of the heart valve repair device within the applicator tube, and wherein the heart valve repair device is advanced to the area of the heart valve with the ventricular winding held in a constrained condition in which it has a relatively straightened shape;

releasing the ventricular winding on an atrial side or a ventricular side of the heart valve, thereby allowing the ventricular winding to assume its unconstrained condition in which it has the generally spiral shape;

after releasing the ventricular winding, positioning the ventricular winding on the ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together, the turning of the ventricular winding being accomplished by using the delivery device to turn the grasping element whereby turning the grasping element results in turning the ventricular winding generally around the axis of the grasping element; and releasing the heart valve repair device from the delivery system by advancing the internal rod distally within the applicator tube, thereby moving the hook distally relative to the applicator tube and releasing the grasping element of the heart valve repair device from the hook;

wherein the heart valve repair device is free of any atrial stabilizing section.

15. The method as in claim 14, wherein the heart valve repair device, including the ventricular winding, comprises a wire, bundle of wires, strip, rod, tube, or a combination thereof.

16. The method as in claim 14, wherein the heart valve repair device is comprised at least in part of a metallic material.

17. The method as in claim 14, wherein the heart valve repair device is comprised at least in part of a shape memory metal material.

18. The method as in claim 14, wherein the heart valve repair device is comprised at least in part of a plastic material.

19. The method as in claim 14, wherein the heart valve repair device is comprised at least in part of a composite material.

20. The method as in claim 14, wherein the heart valve repair device further comprises at least one anti-rotation element.

21. The method as in claim 14, wherein the ventricular winding has an end portion that is angled downwardly.

22. The method as in claim 14, wherein the first leaflet comprises an anterior leaflet of a mitral valve and the second leaflet comprises a posterior leaflet of the mitral valve.

23. The method as in claim 14, wherein the method comprises, after turning the ventricular winding in the first direction, turning the ventricular winding in a second direction such that the captured chords of the first and the second leaflets move further from the center of the ventricular winding, to adjust a positioning of the chords in the device.

24. The method as in claim 14, wherein the steps of positioning the ventricular winding on the ventricular side of the heart valve and turning the ventricular winding in the first direction comprises using the delivery system to turn the ventricular winding in the first direction such that the captured chords of the first and the second leaflets move closer to the center of the ventricular winding.

25. The method of repairing a heart valve comprising:
delivering a heart valve repair device to an area of the heart valve using a delivery system comprising an applicator tube and an internal rod within the applicator tube, the heart valve repair device comprising a ventricular winding that in an unconstrained condition has a generally spiral shape, the generally spiral shape comprising at least a first turn and a second turn wherein at least the first turn is a full turn extending 360 degrees around a center of the ventricular winding, wherein in a radial direction from the center of the ventricular winding the second turn is farther away from the center of the ventricular winding than the first turn, the heart valve repair device further comprising a grasping element that is connected to the center of the ventricular winding and that extends from the center of the ventricular winding, the grasping element having an axis, the internal rod of the delivery system terminating in a hook adapted to hold the grasping element of the heart valve repair device within the applicator tube;

releasing the ventricular winding thereby allowing the ventricular winding to assume its unconstrained condition in which it has the generally spiral shape;

after releasing the ventricular winding, positioning the ventricular winding on a ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together, the turning of the ventricular winding being accomplished by using the delivery device to turn the grasping element whereby turning the grasping element results in turning the ventricular winding generally around the axis of the grasping element; and releasing the heart valve repair device from the delivery system by advancing the internal rod distally within the applicator tube, thereby moving the hook distally relative to the applicator tube and releasing the grasping element of the heart valve repair device from the hook;

wherein the heart valve repair device does not have any part that extends into an atrial side of the valve after implantation and completion of the method.

26. The method of repairing a heart valve comprising:
delivering a heart valve repair device to an area of the heart valve using a delivery system comprising an applicator tube and an internal rod within the applicator tube, the heart valve repair device comprising a ventricular winding that in an unconstrained condition has a generally spiral shape, the generally spiral shape comprising at least a first turn and a second turn wherein at least the first turn is a full turn extending 360 degrees around a center of the ventricular winding, wherein in a radial direction from the center of the ventricular winding the second turn is farther away from the center of the ventricular winding than the first turn, and wherein an overall diameter of the ventricular winding is smaller than a diameter of an annulus of the heart valve, the heart valve repair device further comprising a grasping element that is connected to the center of the ventricular winding and that extends from the center of the ventricular winding, the grasping element having an axis, the internal rod of the delivery system terminating in a hook adapted to hold the grasping element of the heart valve repair device within the applicator tube;

releasing the ventricular winding thereby allowing the ventricular winding to assume its unconstrained condition in which it has the generally spiral shape;

after releasing the ventricular winding, positioning the ventricular winding on a ventricular side of the heart valve and turning the ventricular winding in a first direction such that the ventricular winding captures chords associated with a first leaflet of the heart valve and chords associated with a second leaflet of the heart valve within one generally spiral path defined by the generally spiral shape of the ventricular winding, wherein the generally spiral path extends at least between the first turn and the second turn of the ventricular winding, and such that, by turning the ventricular winding in the first direction, the captured chords of the first and the second leaflets within the generally spiral path are brought toward the center of the ventricular winding, thereby causing the first and the second leaflets of the heart valve to be drawn together, wherein the ventricular winding captures less than all of the chords associated with the heart valve, the turning of the ventricular winding being accomplished by using the delivery device to turn the grasping element whereby turning the grasping element results in turning the ventricular winding generally around the axis of the grasping element; and releasing the heart valve repair device from the delivery system by advancing the internal rod distally within the applicator tube, thereby moving the hook distally relative to the applicator tube and releasing the grasping element of the heart valve repair device from the hook; wherein the heart valve repair device is free of any atrial stabilizing section.

* * * * *